Figure 1:
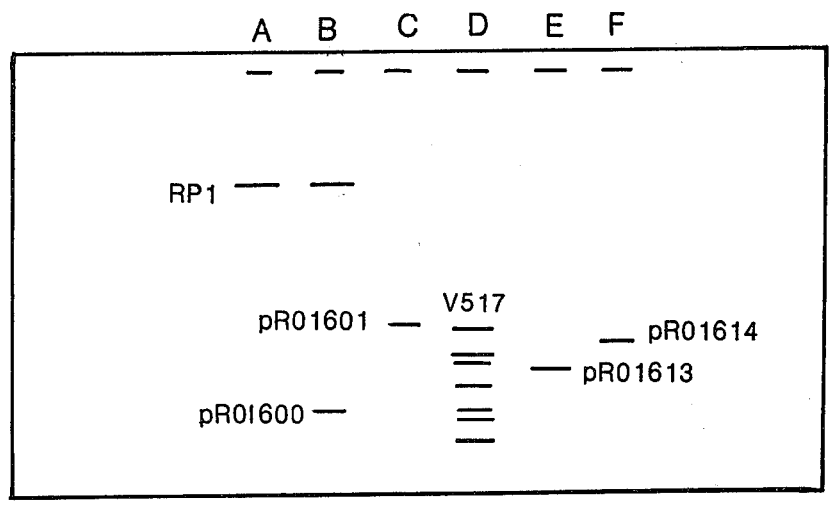

United States Patent [19]

Olsen

[11] 4,374,200

[45] Feb. 15, 1983

[54] BROAD HOST RANGE SMALL PLASMID RINGS AS CLONING VEHICLES

[75] Inventor: Ronald H. Olsen, Ann Arbor, Mich.

[73] Assignee: Microlife Technics, Inc., Sarasota, Fla.

[21] Appl. No.: 147,563

[22] Filed: May 8, 1980

[51] Int. Cl.³ .................... C12N 15/00; C12P 21/00; C12P 21/02; C12P 19/34; C12N 1/20; C12N 1/00; C12R 1/065; C12R 1/22; C12R 1/38; C12R 1/19

[52] U.S. Cl. ..................... 435/172; 435/68; 435/70; 435/91; 435/253; 435/317; 435/831; 435/849; 435/852; 435/874

[58] Field of Search ............... 435/68, 317, 253, 172, 435/91, 70

[56] References Cited

U.S. PATENT DOCUMENTS 4,237,224 12/1980 Cohen et al. .................... 435/68

OTHER PUBLICATIONS

Boyer et al., in Recombinant Molecules: Impact on Science and Society, Beers et al. (eds.), Raven Press, N.Y. (1977), pp. 9–20.
Sutcliffe et al., in Genetic Engineering, Chakrabarty (ed.), CRC Press, W. Palm Beach, Fla., (1978), pp. 83–111.
Olsen et al., J. Bact. 113, 772 (1973).
Grinsted et al., Plasmid 1, 34–37 (1977).
Hansen et al., J. Bact. 135, 227 (1978).
Starlinger et al., in Genetic Engineering, Chakrabarty, (ed.), CRC Press, W. Palm Beach, Fla. (1978), pp. 123, 136, 137.

Primary Examiner—Alvin E. Tanenholtz
Assistant Examiner—James Martinell
Attorney, Agent, or Firm—Ian C. McLeod

[57] ABSTRACT

The present invention relates to novel, broad bacterial host range small plasmid deoxyribonucleic acid rings which serve as cloning vehicles for DNA fragments, particularly those separated from other plasmid rings or from chromosones, recombined with the small plasmid rings and to the processes for recombining the plasmid rings and to processes for transferring them between host bacteria. In particular, the present invention relates to the aggregate plasmid ring RP1/pRO1600, to pRO1600 and plasmid ring derivatives thereof, particularly including pRO1601; pRO1613 and pRO1614, all of which are carried for reference purposes in *Pseudomonas aeruginosa* ATCC 15692 (also known as strain PAO1c) and are on deposit at the Northern Regional Research Laboratories (NRRL) of the U. S. Dept. of Agriculture at Peoria, Ill. The plasmid ring RP1 (also known as R1822) is deposited in *Pseudomonas aeruginosa* NRRL-B-12123 (and is a known plasmid ring). The pRO1600 portion of the aggregate is a new plasmid ring. The novel small plasmid rings are particularly useful for recombinant genetic manipulation wherein the DNA fragments are introduced into the plasmid rings to produce useful, cloneable characteristics in the host bacterium, particularly chemical generating characteristics.

17 Claims, 3 Drawing Figures

A

B

C

D

BROAD HOST RANGE SMALL PLASMID RINGS AS CLONING VEHICLES

SUMMARY OF THE INVENTION

The present invention relates to novel small plasmid rings having a broad bacterial host range and to the processes for recombining the fragments with other DNA fragments in vivo or in vitro and/or for transferring the plasmids between host bacteria. In particular, the present invention relates to plasmid rings which are derivatives of the aggregate plasmid rings RP1/pRO1600 which occurred by chance only once as a result of a mutation in *Pseudomonas aeruginosa* ATCC 15692 during conjugation of the bacteria containing the natural plasmid ring RP1 (also known as R1822). The novel plasmids are referred to herein as pRO16xy wherein x and y are integers.

PRIOR ART

The prior art commercial efforts involving recombinant genetic manipulation of plasmids for producing various chemicals have centered on *Escherichia coli* as a host organism. The reason is that the recombinant plasmids are not compatible with other host organisms. However, *E. coli* is not the most desirable organism to use for these purposes because of concerns about its ability to grow in the intestinal tract in mammals and also because of its ability to produce disease. It would be very desirable to be able to use host bacteria besides *E. coli* with plasmids having a broad bacterial host range. The present invention is concerned with such plasmids. It is particularly concerned with the use of organisms that will not survive at mammalian body temperatures.

The following are definitions used in reference to the present invention.

The phrase "bacterial conjugation" means the mating and genetic transfer between at least two bacterial hosts, the donor being designated as "male" and the recipient as "female".

The phrase "plasmid aggregate" means an association between two plasmid rings wherein each plasmid maintains its structure as a ring and wherein each ring is capable of separate recombinant genetic manipulation.

The term "transport" means any process whereby DNA is transferred from one bacterium to another.

The term "transduction" means DNA plasmids or fragments caused to be transported by bacterial viruses from one bacterium to another in vivo by natural processes.

The term "transformation" means the injection of DNA stripped from a whole bacterial cell in vitro into a host bacterium.

The term "transposition" means the movement of genetic material from one portion of a DNA molecule to another or from one DNA molecule to another.

The term "transposon" refers to the genetic material transferred by transposition.

The phrases "DNA source" or "DNA fragment" means DNA from chromosomal or extrachromosomal cellular elements (such as plasmids) derived from eucaryotic or procaryotic cells and/or their parasites including viruses.

The state of the patent art is generally described in U.S. Pat. Nos. 3,813,316; 4,038,143; 4,080,261; 4,082,613 and 4,190,495. These patents describe prior art processes related to the present invention.

Two elements have been identified as necessary for the replication of a DNA molecule in vivo other than the battery of enzymes and proteins required for synthesis of the DNA molecule per se. They are (1) a region on the DNA molecule which is identified as the origin of DNA replication and which is recognized by a protein and also (2) the gene for this protein which is found on the same DNA molecule. Given this minimum specification for a DNA molecule capable of autonomous self-reproduction in a bacterial cell, additional pieces of DNA may be included insofar as they do not interfere with the two functions identified above. The combination of 1 and 2 above found in nature contained within and maintained extrachromosomally by host bacterial species has been called plasmids or extrachromosomal elements (Bacteriological Reviews, September, pp. 552–590 (1976)). Until recently, microbial geneticists have manipulated DNA fragments in vivo using host bacterial cell recombination mechanisms to recombine DNA from the bacterial chromosome into plasmids or to effect recombination between plasmids co-maintained in the same host bacterium. This practice has allowed purification of various regions of a more complex genome by removal of a portion of the complex genome to another replicating unit. However, this practice does not normally allow for the construction of plasmid-hybrids comprised of DNA from disparate sources or transported across large biological barriers from different organisms.

In recent years, however, techniques for the in vitro manipulation and recombination of heterogeneous fragments of DNA have allowed the construction of hybrid DNA molecules. A brief summary of the in vitro process quoted from *Recombinant Molecules: Impact on Science and Society* R. F. Beers and E. G. Bassett, eds., pp 9–20, Raven Press, New York (1977)) follows.

"There are several important technical components to in vitro recombinant (DNA) technology which ultimately result in the insertion of DNA fragments from any source into replicons (plasmids)—and their recovery as replicating elements in bacteria. These components are:

1. the systematic dissection of the DNA molecules of interest with restriction endonucleases (see Roberts, in *Recombinant Molecules*, for a discussion of these enzymes);
2. the rejoining of DNA fragments by ligation to an appropriate cloning vehicle (or replicon);
3. the transformation of a cell with the recombinant DNA and selection of cells containing the recombinant plasmid; and
4. the identification and characterization of the resulting "cloned" fragment of DNA."

This invention relates to all of the above, paticularly item 2, namely, the requirement for an appropriate cloning vehicle (plasmid) and the novel properties of the plasmid cloning vector described herein contributing to the utility of the transformation process described above.

Biological properties of a plasmid potentially useful for molecular DNA cloning have been summarized by D. R. Helinski et al, in "*Recombinant Molecules: Impact on Science and Society,* p. 151, R. F. Beers and E. G. Bassett, eds., Raven Press, New York (1977)).

"Since the initial demonstration of the utility of a plasmid element for the cloning of genes in *Escher-*

*ichia coli*—a variety of plasmid elements have been developed as cloning vehicles in both *E. coli* and (for different plasmids) in other bacteria. These newer cloning vehicles possess the following plasmid properties that are advantageous for the cloning of DNA:

1. stable maintenance in the host bacterial cell;
2. non-self-transmissibility;
3. ease of genetic manipulation;
4. ease of isolation;
5. the capacity of joining with and replicating foreign DNA of a broad size range;
6. ease of introduction of the in vitro generated hybrid plasmid into a bacterial cell."

The foregoing specifications relating to characteristics considered desirable for the maximum utility of a plasmid useful for recombinant DNA technology, however, do not include a consideration for enhanced utility of a cloning plasmid with a broad bacterial host range.

Most bacterial plasmids described to date can be maintained only in bacterial species closely related to the bacterium from which the plasmid has originally been isolated. Because of this, the requirements associated with the maintenance and duplication of the particular plasmid's DNA generally are specific to the plasmid in question. There have been, however, exceptions to this general observation. For example, Olsen (the inventor herein) and Shipley (Journal of Bacteriology, 113, No. 2, pp. 772–780 (1973)) showed that a plasmid specifying multiple antibiotic resistances, designated R1822 (and later changed to RP1), was transferred to a variety of bacterial species representative of related and unrelated bacterial genera by sexual conjugation. The origin of the strain *Pseudomonas aeruginosa* 1822 from which PR1 was later obtained is set forth in Lowbury, E. J. et al Lancet ii 448–452 (1969). The bacterial host range of the plasmid PR1 includes Enterobacteriaceae, soil saprophytic bacteria (Pseudomonas), *Neisseria perflava*, and photosynthetic bacteria. Plasmid PR1, then, is an example of a broad host range bacterial plasmid which freely transfers among unrelated bacterial species.

The plasmid ring RP1 is relatively large. The large size and composition of this plasmid ring makes the process of bacterial transformation inefficient. It would be a significant improvement in the art to provide a small plasmid ring as a cloning vehicle and recombinants thereof which were easily and widely transportable particularly by transformation, from bacterial host to bacterial host. The plasmids would be particularly useful if they included a single phenotypic marker for antibiotic resistance for identification purposes. It would also be an improvement to provide processes for in vivo or in vitro recombination of fragments of the small plasmid ring with other genetic fragments.

OBJECTS

It is therefore an object of the present invention to provide novel plasmid fragmentation and recombination and/or transport processes. Further it is an object to provide novel recombinant plasmid rings derived from small plasmids which act as cloning vehicles when combined in the recombinant plasmid rings and wherein the plasmid rings have a broad bacterial host transfer range. It is particularly an object of the present invention to provide recombinant plasmid rings which have useful chemical generating properties or some other useful characteristic in the host bacterium. These and other objects will become increasingly apparent by reference to the following description and the drawings.

IN THE DRAWINGS

FIG. 1 is a line drawing of a slab agarose gel electrophoresis patterns for RP1 of the prior art (A), *E. coli* V517 electrophoresis size standard (D) and for RP1/pRO1600 (B) and other plasmids (C, E, F) of the present invention. The longer the pattern, the smaller the plasmid.

Figure 2:
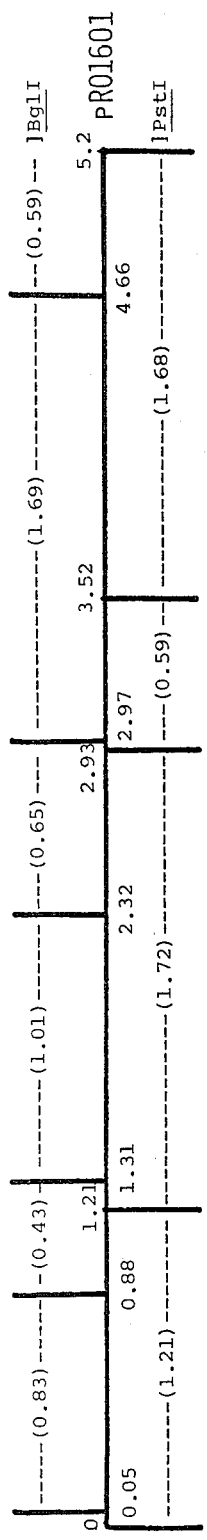
Figure 2:
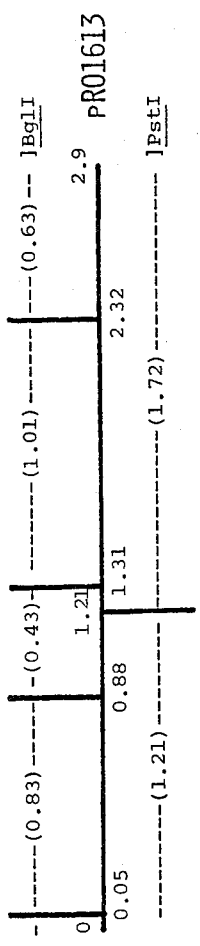
Figure 2:
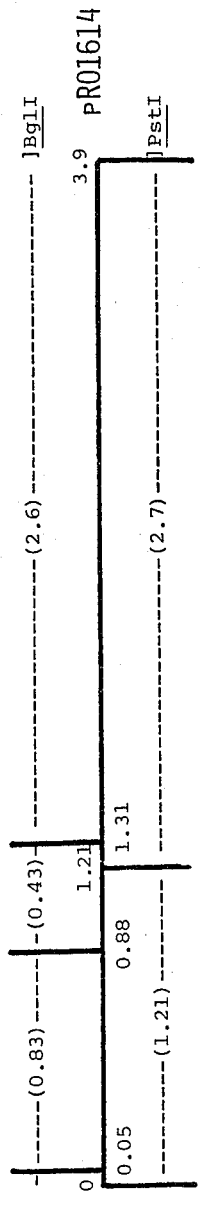
Figure 2:
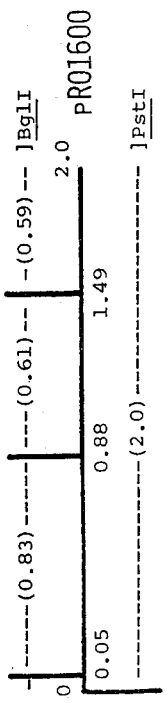

FIG. 2 shows restriction endonuclease PstI and BglI maps in megadaltons (daltons $\times 10^6$) for the preferred plasmids of the present invention, particularly plasmids pRO1601, pRO1613, pRO1614 and pRO1600. Numerical values in parenthesis represent molecular size in daltons $\times 10^6$ for restriction endonuclease fragments. Numerical values above or below the unbroken horizontal line are map distance of the restriction endonuclease recognition site in daltons $\times 10^6$ from zero as defined by the single PstI restriction endonuclease-DNA cleavage site present in plasmid pRO1600.

Figure 3:
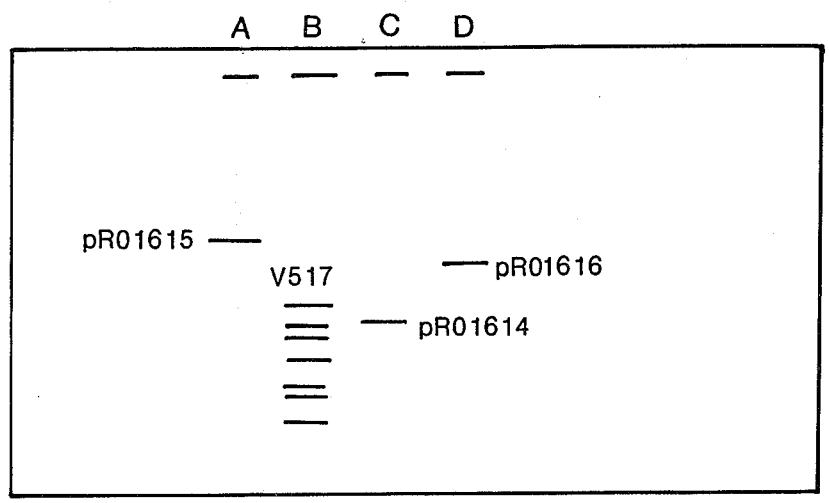

FIG. 3 is a line drawing of a slab agarose gel electrophoresis patterns for: pRO1614 (C); DNA from *E. coli*; V517 of the prior art for reference purposes (B) and DNA from transformant clones capable of growth without L-isoleucine or L-valine (A), referred to as pRO1615, or L-methionene (D), referred to as pRO1616, as a result of the recombinant modification of pRO1614.

GENERAL DESCRIPTION

The present invention relates to a recombinant deoxyribonucleic acid plasmid ring including a first plasmid fragment, the first plasmid being originally derived from a plasmid aggregation with plasmid RP1 and measuring about $2 \times 10^6$ daltons or less in molecular size and having a critical restriction endonuclease BglI digestion fragment measuring $0.83 \times 10^6$ daltons in molecular size which is indispensible for replication, covalently combined with at least one second deoxyribonucleic acid fragment which is a restriction endonuclease digestion fragment ligated to the first plasmid in vitro or a naturally occurring fragment inserted by a bacterium in vivo into the first plasmid as a recombinant plasmid ring capable of being carried by *Pseudomonas aeruginosa* PAO ATCC 15692 (PAO1c) and having a broad bacterial host transmission range, wherein the second fragment contributes a useful chemical characteristic to the recombinant plasmid ring and wherein the plasmid ring clones itself by DNA replication during cell division of the host bacterium.

The present invention also relates to the bacterial composition which comprises a deoxyribonucleic acid plasmid ring including a first plasmid fragment, the first plasmid being originally derived as a plasmid aggregation with plasmid RP1 measuring about $2 \times 10^6$ daltons or less in molecular size and having a critical restriction endonuclease BglI digestion fragment measuring $0.83 \times 10^6$ daltons in molecular size which is indispensible for replication, covalently combined with at least one second deoxyribonucleic acid fragment which is a restriction endonuclease digestion fragment, ligated to the first plasmid in vitro or a naturally occurring fragment inserted by a bacterium in vivo into the first plasmid as a recombinant plasmid ring capable of being carried by *Pseudomonas aeruginosa* PAO ATCC 15692 (PAO1c) and having a broad bacterial host transmission range, wherein the second fragment contributes a useful chemical characteristic to the recombinant plasmid ring and wherein the plasmid ring clones itself by DNA replication during cell division of the host bacterium; and a host bacterium.

The present invention also relates to a process for transporting DNA plasmids to bacterial hosts in vivo using the processes of bacterial conjugation, transformation or transduction, the improvement which comprises transporting a deoxyribonucleic acid plasmid ring, including a first plasmid ring originally derived as a plasmid aggregation with plasmid RP1 measuring about $2 \times 10^6$ daltons or less in molecular size and having a critical BglI restriction endonuclease digestion fragment measuring $0.83 \times 10^6$ daltons in molecular size which is indispensible for replication alone or with a fragment from the first plasmid ring, covalently combined with at least one second deoxyribonucleic acid fragment which is a restriction endonuclease digestion deoxyribonucleic acid fragment ligated to the first plasmid or a naturally occurring fragment inserted by a bacterium in vivo in the first plasmid to form a recombinant plasmid ring, wherein the plasmids are capable of being carried by *Pseudomonas aeruginosa* PAO ATCC 15692 (PAO1c), wherein the plasmids have a broad bacterial host range, and wherein the plasmid clones itself by DNA replication during cell division of the host bacterium.

The present invention relates to the process which comprises providing an aggregate of a first plasmid with a second plasmid, wherein the second plasmid has a transposon which produces a useful chemical characteristic and wherein the first plasmid was originally derived as an aggregation with RP1 and measures about $2 \times 10^6$ daltons or less in molecular size and has a critical BglI endonuclease digestion fragment measuring $0.83 \times 10^6$ daltons in molecular size indispensible for replication; providing the aggregate plasmid in a plasmid receptive bacterial cell; growing the receptive bacterial cell in a growth medium with the aggregate plasmid to randomly produce a recombined plasmid including the transposon and first plasmid, wherein the recombined plasmid replicates upon division of the bacterial cell; and selecting the bacterial cells with the recombined plasmid with the transposon.

Further, the present invention relates to the process for producing recombinant deoxyribonucleic acid plasmids which comprises providing a first plasmid and a second deoxyribonucleic acid source, wherein the first plasmid was originally derived from a plasmid aggregation with plasmid RP1 measures about $2 \times 10^6$ daltons or less in molecular size and has a critical restriction endonuclease BglI digestion segment measuring $0.83 \times 10^6$ daltons in molecular size which is indispensible for replication; reacting the plasmid and the second deoxyribonucleic acid source with at least one restriction endonuclease which cleaves the first plasmid and the second deoxyribonucleic acid source into linear DNA fragments; and randomly recombining the linear deoxyribonucleic acid fragments using ligation to form recombinant plasmids which replicate in a bacterial cell.

Finally, the present invention relates to a deoxyribonucleic acid fragment for forming plasmids, the fragment being formed from a first plasmid originally derived from a plasmid aggregation with plasmid RP1 and measuring about $2 \times 10^6$ daltons or less in molecular size, wherein the fragment has a critical restriction endonuclease BglI digestion fragment measuring $0.83 \times 10^6$ daltons in molecular size which is indispensible for replication in a plasmid. BglI was isolated from *Bacillus globiggi*. BglI produces 5' termini as follows:

The plasmid content of bacteria can be conveniently and expeditiously estimated by employing the technique of slab agarose gel electrophoresis with visualization of the result on photographs of the resulting electropherogram (for example, see Hansen and Olsen, Journal of Bacteriology, 135, No. 1 pp. 227–328 (1978)). Thus DNA was electrophoresed as shown in FIG. 1 as follows: A, DNA extracted from *Pseudomonas aeruginosa* NRRL 12123; B, DNA from RP1/pRO1600; C, DNA from pRO1601; D, DNA from *Escherichia coli* V517, a multi-plasmid-containing strain used as a size standard (Plasmid, 1, pp. 417–420 (1978)); E, DNA from pRO1613; F, DNA from pRO1614. This procedure also allows an estimate of the molecular size of any plasmids present when suitable standards are incorporated into the procedure.

When the plasmid RP1 is caused to transfer from one bacterium to another by the process called bacterial conjugation (or sexual mating), the recipient bacterium that has newly acquired the plasmid normally contains a plasmid that is indistinguishable on electropherograms from the plasmid present in the donor bacterium. In FIG. 1, file A, is depicted the usual appearance of plasmid RP1 when extracted from donor cell populations or a recipient cell population subsequent to its transfer. On one occasion another result was obtained. Analysis of a culture derived from a single recipient cell of ATCC 15692 (strain PAO2) which had received plasmid RP1 in a mating experiment with *Pseudomonas aeruginosa* PAO25 (another mutant variation of ATCC 15692, the same as PAO2 as described above except that it requires leucine and arginine for growth and maintenance and on deposit at the Univ. of Michigan) produced a variant plasmid aggregate. The transconjugant showed the presence of not only the parent plasmid, but also a second and considerably smaller plasmid (FIG. 1, file B). This result has not been seen again after many repetitions of the process. The parental-size plasmid is shown at the top of file B; the anomolous smaller plasmid appears at the lower portion of the electropherogram depicted in FIG. 1. The size of the lower plasmid, estimated by comparison and calculation relative to the size standards in file D, is $2 \times 10^6$ daltons compared to $38 \times 10^6$ daltons for RP1. The appearance of the small plasmid, then, reflects a novel event which, in general terms, may be considered a random mutational event which most likely occurred during the transfer to the recipient bacterium of the parental plasmid, RP1. I have designated the small plasmid pRO1600 and the aggregation with RP1 as RP1/pRO1600.

The utility of a small plasmid for application in recombinant DNA technology derives, in part, from its ability to encode genetic information for a unique metabolic trait not possessed by the host bacterium. Accordingly, the presence or absence of the plasmid, subsequent to genetic manipulations, can be determined on the basis of the presence or absence of the metabolic trait in question. Preliminary analysis of the bacterial strain shown in FIG. 1, file B showed no unique metabolic trait (phenotypic character) associated with the presence of plasmid pRO1600. I therefore applied standard bacterial genetic techniques to add a distinctive phenotypic trait to pRO1600 allowing its detection in later experiments whereby I tested its ability to be transformed from partially purified DNA solutions to recipient bacterial strains. The distinctive phenotypic trait added was a piece of DNA which encodes genetic information for resistance to the antibiotic, carbenicillin. Accordingly, all bacteria maintaining plasmid pRO1600 with this piece of DNA will grow in the presence of carbenicillin unlike the parental, plasmid-free, bacterial strain.

The genetic trait for carbenicillin resistance was added to plasmid pRO1600 by the genetic process called transposition. Some antibiotic resistance genes, called transposons, are able to move from one location to another on a piece of DNA or alternatively, able to move from one DNA molecule to another within the bacterial cell by the genetic process called transposition (S. Cohen, "Transposable genetic elements and plasmid evolution" Nature, 263, pp. 731–738 (1976)). These genetic elements accomplish this process in the absence of bacterial host genetic recombinational mechanisms. Plasmid RP1, shown in file A, FIG. 1, contains a transposon called Tn1 which encodes genetic information for resistance to carbenicillin and related antibiotics (penicillin, ampicillin). Transposon, Tn1 is a transposable genetic element of $3.2 \times 10^6$ daltons molecular size. Accordingly, DNA molecules that have been transposed by Tn1 would increase in size by $3.2 \times 10^6$ daltons.

Transposition occurs randomly in populations of bacterial cells which all contain a donor DNA molecule which has the transposon. Thus, in the case of bacterial strain Pseudomonas aeruginosa RP1/pRO1600, one would expect a small proportion of the bacterial cells to contain transposed-variant plasmids. For example, as shown in file B, FIG. 1, a few bacterial cells in the culture would contain a DNA molecule larger by $3.2 \times 10^6$ daltons than the small DNA molecule shown at the bottom of the electropherogram (the plasmid designated pRO1600.) The relatively small number of these bacteria in the culture, however, precludes their detection on agarose gels as shown in FIG. 1. However, these transposed derivatives of plasmid pRO1600 can be detected and isolated by using the genetic technique called bacterial transformation. By this process, DNA that has been extracted from cells called donors is added to a plasmid-free recipient bacterial cell culture. The admixture, in turn, is then grown on bacteriological medium containing, in this instance, the antibiotic carbenicillin. Under these conditions, only bacterial cells that have taken up and replicated a genetic element which encodes genetic information for the antibiotic carbenicillin will grow to dense populations. When this experiment is done, two types of carbenicillin resistant bacterial strains would be expected: those which have received all of the donor parent plasmid, RP1; those which have only received pRO1600 combined with the transposon which encodes carbenicillin resistance, Tn1, which is now contained within its structure. The former class of possible bacterial isolates can be distinguished by the fact that these cells will be resistant to not only carbenicillin, but also tetracycline and kanamycin, other genes which are part of the structure of RP1. In the case of the latter possibility; however, these bacterial isolates would only demonstrate resistance to the antibiotic, carbenicillin, since they have only received Tn1 which has jumped from plasmid RP1 to plasmid pRO1600 co-maintained at the same time in a bacterial cell. Such a bacterial strain was obtained by the process described above and its DNA, following extraction of its plasmid and electrophoresis is shown in file C, FIG. 1. This plasmid, designated pRO1601, shows slower electrophoretic mobility than plasmid pRO1600 reflecting its larger size. When calculations are done using the standard DNA depicted in file D, FIG. 1, it is determined that pRO1601 is larger than pRO1600 by $3.2 \times 10^6$ daltons molecular size. This relationship, then, suggests that Tn1 has been added to pRO1600 and accordingly a unique metabolic trait (phenotypic marker) has been added to pRO1600 allowing its detection by testing for resistance to the antibiotic, carbenicillin.

DNA molecules are linear polymers comprised of substituent molecules called purines and pyrimidines. The exact linear sequence of joined purines or pyrimidines, then, defines any region of a DNA molecule of interest. Analagous regions of any DNA molecule can be detected by their cleavage with unique enzymes specific in their activity on those regions called Class II restriction endonucleases (B. Allet, "Fragments produced by cleavage of lambda deoxyribonucleic acid with Haemophilus parainfluenzae restriction enzyme HpaII" Biochemistry, 12, pp. 3972–3977 (1972)). The specific regions of a DNA molecule, called recognition sequences, which serve as sites for cleavage by any of more than 40 specific restriction endonucleases will be distributed differently or absent when DNA from different biological sources is compared. Conversely, related or identical DNA molecules will yield an identical set of fragments, subsequent to restriction endonuclease digestion and analysis by the techniques of slab agarose gel electrophoresis. Therefore new plasmids can be produced subsequent to digestion as described above. If the size of the DNA molecule is small, and the number of fragments generated by treatment with restriction endonuclease enzyme is few, these fragments can randomly associate in different order than originally present on the parent molecule. Following this random re-association, the fragments can be again covalently joined when the re-associated complex is treated with a second enzyme called DNA ligase and required co-factors. The foregoing process, then, can be applied to the analysis of structure of DNA molecules and production of new combinations of DNA sequences. By the foregoing process, then, plasmid structure can be altered by deleting non-essential regions of DNA or the production of a DNA molecule comprised of DNA from biologically unrelated sources.

The present invention particularly relates to plasmid pRO1601, its modification and its utility for genetic cloning and novelty by applying the rationale and procedures described in general terms above and commonly referred to as recombinant DNA technology. The essential features of this recombinant DNA technology have been summarized previously (S. Cohen, Scientific American, July, pp. 25–33 (1975)).

Analysis of plasmid pRO1601 DNA (restriction endonuclease mapping) by conventional procedures referenced above produced the structure depicted in FIG. 2, part A. Inspection of this genetic map shows the presence of four restriction endonuclease recognition sites for the restriction endonuclease, PstI. Transposon, Tn1, which was added to pRO1600 to produce pRO1601 is known to contain 3 PstI restriction endonuclease sites (J. Grinsted et al, Plasmid, 1, pp, 34–37 (1977)). Therefore, the pRO1600 region of the recombinant plasmid that has undergone transposition by Tn1 must contain a single PstI site. Also, since the size of the PstI fragments associated with Tn1 has been estimated (see above ref.), the particular site for PstI cleavage which is unique to pRO1600 can be identified. This site has been chosen as the reference site for mapping and appears at the left of the drawing shown in part A, FIG. 2. Other sites, representing regions of the recombinant plasmid, pRO1601, which are part of Tn1, have been juxtaposed in relation to the pRO1600 PstI site. Also shown on this genetic map are specific recognition sites for the restriction endonucleases BglI. These were determined by comparing other variants of Tn1-transposed plasmid pRO1600 which differed from pRO1601 with respect to the point of the insertion of the transposon Tn1 into pRO1600. For this, conventional procedures attendant to recombinant DNA technology were used.

The PstI restriction endonuclease site drawn at 1.21 on panel A, FIG. 2 which is known to be part of the region reflecting the addition of the transposon, Tn1, is known to be in the middle of the genetic region which encodes for resistance to carbenicillin. Accordingly, insertion of extra DNA at this point will destroy the contiguity of the DNA sequence and result in the loss of the ability of this region of the DNA to specify the enzyme associated with carbenicillin resistance. To demonstrate the utility of pRO1601 for molecular cloning, a piece of DNA was inserted into this site. This piece of DNA, however, contains genetic information for resistance to the antibiotic tetracycline. Consequently, if this piece were incorporated into plasmid pRO1601 at this site, ligated to form a closed circular DNA structure, transformed into a recipient bacterium and cultured with selection for the ability to grow in the presence of tetracycline, cloning of the inserted fragment would have occurred.

The source of DNA for these experiments was yet another plasmid called pBR322 (F. Bolivar et al, "Construction and Characterization of new cloning vehicles II. a multipurpose cloning system" Gene, 2, pp. 95–113 (1977)). Plasmid pBR322, typical of cloning plasmids developed to date, is unable to be maintained in bacteria not closely related to the bacterium of its origin, *Escherichia coli*. Consequently, when this plasmid DNA is introduced into an unrelated bacterium, *Pseudomonas aeruginosa*, it will not confer the ability to grow in the presence of antibiotics for which it encodes resistance, namely, resistance to carbenicillin and tetracycline. If, on the other hand, plasmid pBR322 DNA becomes part of the structure, by recombination, of a plasmid such as plasmid pRO1601, its genetic functions will be conferred to the recombinant plasmid-containing pRO1601-pBR322 hybrid. Plasmid pBR322, analagous to plasmid pRO1601, also contains a gene specifying resistance to the antibiotic, carbenicillin. This gene too has a site for restriction endonuclease PstI within the region of its DNA associated with carbenicillin resistance. To test the assumption that part of the carbenicillin resistance gene of plasmid pRO1601 could be matched up with part of the analogous gene from plasmid pBR322 resulting, in this case, in the conservation of carbenicillin resistance for a hybrid molecule joined in one place at this juncture, I cleaved both plasmid pRO1601 and plasmid pBR322 DNA with the restriction endonuclease PstI. This produces two linear molecules from the parent circular structures which can randomly associate: one of four possible pieces from plasmid pRO1601 and a linear single piece of DNA derived from plasmid pBR322. Following the application of recombinant DNA technology, namely, plasmid cleavage, ligation and transformation with selection for the acquisition of resistance to tetracycline, two groups of recombinant plasmids were obtained as judged later by mapping with restriction endonucleases. These structures are shown in FIG. 2, panels B and C. They have been designated, respectively, pRO1613 and pRO1614.

The structure determined for plasmid pRO1613 conforms to that expected from the following possibilities: reassocation of plasmid pRO1601 PstI fragments depicted on FIG. 2, panel A as traversing the distance between 0 and 1.21 and between 1.21 and 2.93. However, theoretically, this produces a plasmid having two PstI sites not one as shown on FIG. 2, Panel B, for the resultant plasmid, pRO1613. Therefore, it is probable, based on precedent from other systems, that the DNA at 0 and 2.93 on the pRO1601 map has been altered by unknown factors during the process which effected the deletion of a PstI site but still allowed reformation of a closed ring structure required for survival of the plasmid by a bacterium and its progeny cells during growth and reproduction of the bacterial culture. Plasmid pRO1613 has potential utility for the cloning of restriction endonuclease PstI generated fragments of DNA whose presence can be ascertained by the embodiment within the cloned piece of DNA of a metabolic trait for which recombinant progeny can be selected.

The structure determined for plasmid pRO1614 conforms to that expected for a hybrid-recombinant plasmid which contains a part of the cloning vector plasmid, pRO1601, and the cloned fragment, in this case, plasmid pBR322. Furthermore, the formation of this recombinant plasmid, pRO1614, and its transformation into *Pseudomonas aeruginosa* is accomplished by the occurrence of bacteria which are now both carbenicillin resistant and tetracycline resistant. Clearly, then, as hypothesized above, part of the carbenicillin resistance gene has been derived from plasmid pRO1601 (region to the left of the PstI site shown at 1.21) and part of the carbenicillin gene has been derived from the inserted DNA fragment (region to the right of 1.21, FIG. 2, Panel C,) which is part of plasmid pBR322. This result, then, has demonstrated the utility of plasmid pRO1601 for cloning unrelated DNA (plasmid pBR322). This result also demonstrates the derivation of related, albeit size-reduced, derivative plasmids of greater utility than the parent plasmid DNA molecule, pRO1601.

Additional information regarding the essential features of plasmid pRO1601 required for maintenance by a host bacterium is also provided here by these experiments: the region on FIG. 2, Panels A, B and C from 0.05 to 0.88 map units, measuring 0.83 megadaltons is common to all plasmids shown. Accordingly, this is the region of plasmid DNA present originally on plasmid pRO1600 which is essential for the replication and maintenance of the plasmid cloning vector and its possible derivatives. This region, defined by its restriction endonuclease restriction enzyme sites at 0.05 and 0.88 map units is a critical embodiment of this invention.

In addition to the foregoing, restriction endonuclease digest analysis of plasmids described in the development of the invention allow deduction of the genetic map of plasmid pRO1600 is independent of RP1. Its restriction endonuclease digest map is shown in panel D, FIG. 1.

The present invention particularly relates to the process which comprises the addition of chromosome DNA fragments produced by chromosome cleavage with a restriction endonuclease into a broad host range replicator plasmid and its apertinent DNA which has also been cleaved by the same restriction endonuclease. This admixture of plasmid and chromosome DNA fragments is then followed by ligase treatment and transformation of recombined DNA to a suitable bacterial host.

The source of DNA for this series of cloning experiments was plasmid pRO1614 and the *Pseudomonas aeruginosa* strain PAO chromosome. The purpose of these experiments was to demonstrate the utility of pRO1614 for cloning chromosomal DNA fragments corresponding to genetic locations on the chromosome associated with specific metabolic functions contributing to the biosynthetic activities of the bacterial cell. For this purpose of mutant of *P. aeruginosa* designated strain PAO236 (D. Haas and B. Holloway, Molecular and general genetics 144:251 (1976)) was used as the transformation-cloning recipient. Unlike the parent bacterial *P. aeruginosa* strain, PAO 1c (ATCC 15692), strain PAO236 has been mutated to require the addition of the amino acids L-isoleucine, L-valine and L-methionine to growth medium to support cellular synthesis and growth. These nutritional requirements for the amino acids, then, allow for the selection of recombinant clones which contain chromosomal DNA fragments associated with synthesis of these compounds: bacteria which have received the appropriate cloned DNA fragment acquire the ability to grow in the absence of the amino acid for which its biosynthesis has mutated to a requirement. It also follows from the application of this rationale that the recombinant plasmid, in this instance pRO1614 plus the cloned chromosomal DNA fragment, will be larger than the molecular size of plasmid pRO1614 reflecting the acquisition of additional DNA in the molecular cloning process. Within the DNA of plasmid pBR322 cloned into the broad bacterial host range replicator plasmid, pRO1613, is contained the genetic information which specifies resistance to the antibiotic, tetracycline. Within this region of the cloned fragment is also the recognition site for the restriction endonuclease, BamH1. It follows from this relationship, then, that interruption of the contiguity of this tetracycline resistance gene by the in vitro insertion of a cloned DNA fragment will destroy tetracycline resistance specified by this gene. Additionally, if the selection for cloned DNA fragments is on the basis of the acquisition of a specific metabolic trait, bacteria which have received the appropriate recombinant plasmid will grow in the absence of the metabolite corresponding to the specific metabolic trait in question. Such bacterial strains, were obtained by the process described above and their DNA, following extraction of their plasmids are shown in FIG. 3. In FIG. 3, file B contains reference DNA used as a size standard, file C shows plasmid pRO1614, file A shows plasmid pRO1614 with its DNA fragment now allowing growth of bacterial strain PAO236 in the absence of the amino acids isoleucine and L-valine, referred to as pRO1615, and file D shows plasmid pRO1614 with its cloned DNA fragment now allowing growth of bacterial strain PAO236 in the absence of the amino acid L-methionine, referred to as pRO1616. Clearly, the recombinant plasmids shown in files A and D are larger than pRO1614. This is the expected relationship associated with the acquisition of a heterologous DNA fragment following the application of recombinant DNA technology.

SPECIFIC DESCRIPTION

1. Steps

The specific process for developing the genetic cloning plasmid into the form of an artificial, chemically derived, non-transmissible plasmid and its use for the genetic cloning of a representative fragment of DNA is as follows:

(1) Recognition of the novelty and potential usefulness of a mutant plasmid during routine analysis for the presence of the progenitor plasmid, RP1, subsequent to a genetic trasfer experiment: (occurrence of pRO1600);

(2) The addition of a distinctive phenotypic trait for resistance to the antibiotic, carbenicillin, to the small plasmid observed as an extra anamolous plasmid (production of plasmid pRO1601);

(3) Physical mapping of plasmid pRO1601 with restriction endonucleases:

(4) Size-reduction of plasmid pRO1601 (production of plasmid pRO1613), genetic cloning of plasmid pBR322 into plasmid pRO1601 (production of plasmid pRO1614).

(5) Genetic cloning, using recombinant DNA technology, of bacterial chromosome DNA associated with growth by strain PAO236 in the absence of L-isoleucine and L-valine or L-methionine.

2. Strains Used

Bacterial strains used in the development and characterization of plasmids for genetic cloning and their saliant features are as follows:

(1) *Pseudomonas aeruginosa* PAO2. This bacterial strain is a mutant of *P. aeruginosa* 1c (ATCC No. 15692) which has been mutated to require the amino acid, serine, for its growth and maintenance;

(2) *P. aeruginosa* PAO2(RP1). This strain was derived from the foregoing bacterial strain PAO2 by the addition of plasmid RP1 by the process of bacterial conjugation from PAO 2 (RP1) NRRL-B-12123 previously described;

(3) *Pseudomonas putida* PPO131. This bacterial strain is a mutant of *P. putida* A.3.12 (ATCC no. 12633) which has been mutated to require the amino acid, histidine, for its growth and maintenance;

(4) *Pseudomonas fluorescens* PRO141. This isolate was derived from a wild-type strain isolated from nature. The clone of this strain was influenced by its inability to grow and reproduce at temperatures exceeding 32° C. Accordingly this physiological trait effectively contains growth of the bacterium and hence its plasmids to environments excluding mammilian environments. *P. fluorescens* PRO141 is a mutant of the wild-type strain which requires the amino acid, histidine, for growth and maintenance.

(5) *Escherichia coli* ED8654. The strain was derived from *E. coli* K12 and requires the amino acid, methionine, for its growth and maintenance. It has also been mutated to not restrict or modify DNA.

(6) *Azotobacter vinelandii* AVM100. This is a strain isolated from nature.

(7) *Klebsiella pneumoniae* KPO100. This is a strain isolated from nature.

(8) *Pseudomonas aeruginosa* PAO236. This bacterial strain is a mutant of *P. aeruginosa* 1c (ATCC No. 15692) which has been mutated to require the amino acids isoleucine, valine and methionine and other amine acids.

All of the cultures are maintained in the culture collection of the Department of Microbiology, University of Michigan Medical School and are freely available to qualified recipients. Such cultures are also available from other depositories.

3. Materials

The bacteriological medium used for routine maintenance and propagation of the above bacterial strains contained the following ingredients:

| | |
|---|---|
| Bacto-tryptone | 5 g |
| Bacto-yeast extract | 3.75 g |
| Dextrose | 1 g |
| KNO$_3$ | 4 g |
| Distilled Water | 1000 ml |

When solid medium was used, Bacto-agar was added (15 g) prior to sterilization. Medium was sterilized by autoclaving at 121° C. for 15 minutes. Antibiotic was added to the above medium after sterilization and cooling to 50° C. The plasmid DNA was added to recipient bacterial cells and then selected for uptake and maintenance of the plasmid which specified resistance to an antibiotic. For carbenicillin it was 0.5 mg per ml; for tetracycline it was 0.025 mg per ml except for *P. aeruginosa* PAO2. For this bacterial strain, tetracycline was added at 0.05 mg per ml medium.

4. Temperatures

Experiments utilizing *P. putida* or *P. fluorescens* were carried out at 25° C. All other experiments were carried out at 37° C.

EXAMPLE 1

Addition of a selectable genetic marker to plasmid pRO1600 (production of plasmid pRO1601).

For this example a partially purified DNA suspension derived from *P. aeruginosa* PAO2 (RP1) or from *P. aeruginosa* (RP1/pRO1600) was added to a growing culture of *P. aeruginosa* PAO2. Following experimental manipulations attendant to the generally known process of bacterial transformation, the admixture was deposited on the surface of solid medium which contained the antibiotic, carbenicillin. This was incubated at 37° C. for 24 hours and the number of bacterial colonies counted. The results of a typical experiment are shown below in Table 1. These colonies, selected for the ability to grow in the presence of carbenicillin, were then sub-propagated (grown out) on nutrient medium containing either the antibiotic tetracycline or the antibiotic kanamycin to score for the co-nonselected acquisition of phenotypic markers other than carbenicillin resistance which were present in the bacteria used to prepare the transforming DNA.

TABLE 1

| Source of Transforming DNA | Number of Transformants | Nonselected markers which Were Acquired by 100 Transformant colonies | |
|---|---|---|---|
| | | Tetracycline | Kanamycin |
| *P. aeruginosa* PAO2 (RP1) | 190 | 100% | 100% |
| *P. aeruginosa* (RP1)pRO/1600 | 397 | 92% | 92% |

The results shown in Table 1 indicate that 8 percent of the transformants obtained from the *P. aeruginosa* PAO2 (RP1/pRO1600) DNA suspension acquired resistance to carbenicillin only and not resistance to tetracycline or kanamycin. This result, then, suggests that pRO1600 with a Tn1 transposon has been transformed as suggested in the foregoing background discussion. On the other hand, transformants derived from the use of the *P. aeruginosa* PAO2(RP1) DNA suspension, as expected, produced no transformants resistant to carbenicillin only, since this strain does not contain plasmid pRO1600 as a potential transposon acceptor plasmid.

EXAMPLE 2

Size-reduction of plasmid pRO1601 (production of plasmid pRO1613) and cloning of pBR322 DNA into plasmid pRO1601 (production of plasmid pRO1614).

For this experiment, partially purified DNA solutions identified in the Table 2 were treated with enzymes listed. Transformants were selected using *P. aeruginosa* PAO2 bacterial cells that had not previously received a plasmid. The antibiotic resistance(s) acquired by the bacteria as a consequence of their admixture with the various DNA preparations, treated as indicated, are shown on the right column of the Table.

TABLE 2

| Plasmid DNA Used | Treatment of DNA | Number of Transformants | Transformant Phenotype |
|---|---|---|---|
| pBR322 | None | 0 | Not Relevant |
| pBR1601 | None | 69,000 | carbenicillin resistant |
| pRO1601 | PstI digestion + ligation | 70 | carbenicillin resistant pRO1613 |
| pRO1601 + pBR322 | PstI digestion + ligation | 2 | carbenicillin resistant, |
| | | 4 | carbenicillin and tetracycline resistant pRO1614 |

Also noteworthy from the above experiments is the failure of plasmid pBR322, by itself to transform. Therefore, the expression of its tetracycline resistance, when cloned into plasmid pRO1601 reflects its maintenance by virtue of its association with critical functions provided by the vector, plasmid pRO1601.

EXAMPLE 3

Demonstration of borad bacterial host range of plasmids derived from pRO1600.

To demonstrate the utility of derivatives of plasmid pRO1600 (pRO1613, pRO1614) with respect to the usefulness of this invention for conducting cloning experiments using recombinant DNA technology in bacteria of disparate ecological niche and physiological properties, bacterial transformation studies were done using bacteria other than *P. aeruginosa* PAO2 as the transformation-recipient bacterium. The results of typical experiments are shown below in Table 3. The procedure for producing and exacting the DNA is described in Hansen and Olsen referred to above.

For this work, approximately 0.5 micrograms of DNA suspended in 0.025 ml buffer solution was added to approximately $1 \times 10^8$ bacterial recipient cells in a volume of 0.2 ml. The solution was heat cycled between 0° and 45° C. using a procedure described in *Transformation of Salmonella typhinium by Plasmid Deoxyribonucleic Acid*, J. Bact. Vol. 119 pp. 1072 to 1074 (1974) D. E. Lederburg and S. N. Cohen. This admixture, following experimental manipulation attendant to the known technique of bacterial transformation, was deposited on the surface of solid medium which contained antibiotic. This was incubated at 37° C. for 48 hours at the appropriate temperature and the number of bacterial colonies counted. The results of these experiments are shown in Table 3.

TABLE 3

| Source of Transforming DNA | Transformation-Recipient Bacterial Strain | Selective Antibiotic | Number of Transformants* |
|---|---|---|---|
| pRO1613 | P. aeruginosa PAO2 | Carbenicillin | 132,000 |
| pRO1614 | P. aeruginosa PAO2 | Tetracycline | 38,000 |
| pRO1614 | P. putida PPO131 | Tetracycline | 960 |
| pRO1614 | P. fluorescens PFO141 | Tetracycline | 24,600 |
| pRO1614 | E. coli ED8654 | Tetracycline | 5,500 |
| pRO1614 | K. pneumoniae KPM100 | Tetracycline | 1,300 |
| pRO1613 | A. vinlandii AVM100 | Carbenicillin | 176 |

*out of $10^8$ potential recipient cells

The experiments shown above in Table 3, clearly indicate the broad host range feature of plasmids derived from plasmid pRO1600. Variation in the efficiency of the transformation process with the bacterial strain used, in all probability, is associated with the use of a transformation process which is not optimal for the bacterial strain in question. Accordingly, quantitative aspects of these results do not limit the utility of plasmid pRO1600-derivatives for genetic cloning experiments with bacteria showing poor transformation efficiencies. In these instances, improvements in the process of bacterial transformation for the particular bacterial strain in question should, in the future, enhance the efficiency of transformation per se using these bacterial strains.

EXAMPLE 4

Demonstration of the molecular cloning of chromosomal DNA from *Pseudomonas aeruginosa* using the recombinant plasmid, pRO1614.

To demonstrate the utility of the derived plasmid, pRO1614, with respect to the usefulness of this invention for conducting cloning experiments using recombinant DNA technology in bacteria for the cloning of bacterial chromosome genes, a cloning experiment was done for the selection and isolation of bacterial genes associated with the biosynthesis of the amino acids L-isoleucine, L-valine and L-methionine. The procedure for producing chromosomal and plasmid DNA is described in Hansen and Olsen referred to above.

For this work, approximately 0.5 micrograms of either chromosomal DNA extracted from PAO 1c or plasmid pRO1614 DNA were suspended in 0.025 ml buffer and digested with the restriction endonuclease, BamH1. The separate solutions were then mixed and treated with the enzyme T4 ligase and cofactors. This admixture, following experimental manipulation attendant to the technique of bacterial transformation, was deposited on the surface of solid medium which was supplemented with the nutrients required for growth by *Pseudomonas aeruginosa* for growth except in one instance the amino acids L-isoleucine and L-valine and in another instance, the amino acid L-methionine. A single colony of bacterial growth appeared on each of the above selective medium. (A frequency of one in $10^8$ recipients). When these recombinant DNA plasmids are extracted from transformation recipient bacteria, the resulting DNA shows high transformation frequencies when tested by retransformation into yet another recipient. The frequency for amino acid biosynthesis acquisition corresponds to the frequency for the acquisition of carbenicillen resistance in these experiments. These colonies were then purified and grown up for the production of plasmid DNA.

FIG. 3 shows slab agarose gel electrophoresis portions for plasmid DNA from *Pseudomonas aeruginosa* PAO236. Bacterial cells were grown in nutrient broth medium and plasmid DNA was extracted and processed as described in reference to FIG. 1. DNA was electrophoresed and samples were as follows: A, DNA extracted from a transformant clone capable of growth without L-isoleucine or L-valine (pRO1615); B, DNA from *Escherichia coli* V517, a multi-plasmid-containing strain used as a size standard; C, DNA from *Pseudomonas aeruginosa* PAO2(pRO1614); D, DNA extracted from a transformant clone capable of growth without L-methionine (pRO1616). The estimated molecular sizes for the recombinant plasmids are $14 \times 10^6$ daltons for the plasmid in file A; $10.4 \times 10^6$ daltons for the plasmid in file D.

Recombinant clones for isoleucine and valine biosynthesis (file A) or methionine biosynthesis (file D) are clearly larger than the plasmid pRO1614 cloning vector (file C). This relationship reflects the acquisition, using recombinant DNA technology of chromosomal DNA directing the biosynthesis of the amino acids in question. The recombinant plasmid maintained carbenicillin resistance as expected.

The novel plasmids of the present invention and RP1 have been deposited for reference purposes with the Northern Regional Research Laboratory and are freely available upon request by number. The plasmids in *Psuedomonas aeruginosa* are also available from the Univ. of Michigan, Ann Arbor, Mich. by internal reference numbers:

| Internal Reference | NRRL Reference |
|---|---|
| RP1 | B-12123 |
| pRORP1/1600 | B-12124 |
| pRO1601 | B-12125 |
| pRO1613 | B-12126 |
| pRO1614 | B-12127 |
| pRO1615 | B-12149 |
| pRO1616 | B-12148 |

It should be recognized that there are many experiments that might be performed which will occur to those skilled in the art. It will be recognized that there are legal restraints to such experiments and in any event they will be obvious to those skilled in the art.

I claim:

1. The process for producing recombinant deoxyribonucleic acid plasmids which comprises:
   (a) providing a first plasmid as a cloning vehicle selected from pRO1600, pRO1601, pRO1613, pRO1614, pRO1615, and pRO1616 as carried in *Pseudomonas aeruginosa* NRRL-B-12124 NRRL-B-12125, NRRL-B-12126, NRRL-B-12127, NRRL-B-12149 and NRRL-B-12148, respectively;
- (b) reacting the first plasmid and a second deoxyribonucleic acid source with at least one restriction endonuclease which cleaves the first plasmid and the second deoxyribonucleic acid source into linear DNA fragments; and
- (c) randomly recombining the linear deoxyribonucleic acid fragments using ligation to form recombinant plasmids which replicate during cell division when provided in a bacterial cell, wherein deoxyribonucleic acid from the cloning vehicle controls replication of the recombinant plasmid during cell division.

2. The process of claim 1 wherein the second deoxyribonucleic acid source is a plasmid.

3. The process of claim 1 wherein the second deoxyribonucleic acid source is a chromosome.

4. The process of claim 1 wherein the restriction endonuclease is PstI and ligation is accomplished using T4 ligase or derivatives thereof.

5. The process of claim 1 wherein in addition the recombinant plasmids are transformed using a plasmid receptive bacterium and wherein the recombinant plasmids in the bacterium are selected for a particular chemical generating characteristic.

6. In a process for transporting DNA plasmids to bacterial hosts in vivo using the processes of bacterial conjugation, transformation or transduction the improvement which comprises:
   transporting a DNA plasmid ring selected from (a) a first plasmid as a cloning vehicle selected from pRO1600, pRO1601, pRO1613, pRO1614, pRO1615, and pRO1616 as carried in *Pseudomonas aeruginosa* NRRL-B-12124, NRRL-B-12125, NRRL-B-12126, NRRL-B-12127, NRRL-B-12149 and NRRL-B-12148, respectively, and (b) recombinant plasmid ring derivatives of the first plasmid produced by endonuclease cleavage of the first plasmid and a second deoxyribonucleic acid source into linear DNA fragments and then ligation of the fragments together to form the recombinant plasmids wherein the plasmid ring is capable of being carried by *Pseudomonas aeruginosa* PAO ATCC 15692, wherein the plasmid ring has a broad bacterial host range, wherein the plasmid ring clones itself by DNA replication during cell division of the host bacterium and wherein deoxyribonucleic acid from the cloning vehicle controls replication of the recombinant plasmid during cell division.

7. The process of claim 6 wherein the first plasmid ring segment combined with the second DNA segment as the recombinant plasmid ring has a phenotypic marker which imparts selected antibiotic resistances to the host bacterium.

8. The process of claim 7 wherein the antibiotic resistance is to the antibiotic carbenicillin and wherein the plasmid is pRO1601.

9. The process of claim 8 wherein the plasmid pRO1601 is carried in *Pseudomonas aeruginosa* NRRL-B-12125.

10. The process of claim 7 wherein the resistance is to the antibiotics carbenicillin and tetracycline and the plasmid is pRO1614.

11. The process of claim 10 wherein the plasmid is carried in *Pseudomonas aeruginosa* NRRL-B-12127.

12. The process of claim 6 wherein the plasmid is pRO1613.

13. A plasmid cloning vehicle selected from pRO1601, pRO1613, pRO1614, pRO1615, and pRO1616 as carried in *Pseudomonas aeruginosa* NRRL-B-12125, NRRL-B-12126, NRRL-B-12127, NRRL-B-12149 and NRRL-B-12148, respectively.

14. A host bacterium containing a plasmid cloning vehicle selected from pRO1601, pRO1613, pRO1614, pRO1615, and pRO1616 as carried in *Pseudomonas aeruginosa* NRRL-B-12125, NRRL-B-12126, NRRL-B-12127, NRRL-B-12149 and NRRL-B-12148, respectively.

15. A bacterium of claim 14 wherein the host bacterium is selected from Pseudomonas, Escherichia, Azotobacter and Klebsiella.

16. A plasmid having a BglI segment measuring $0.83 \times 10^6$ daltons in molecular size derived from pRO1600 as carried along with RP1 in *Pseudomonas aeruginosa* NRRL-B-12125 combined with a second deoxyribonucleic acid segment, wherein the plasmid derived from pRO1600 replicates itself upon cell division of the host bacterium because of deoxyribonucleic acid from pRO1600.

17. A host bacterium including a plasmid having a BglI segment measuring $0.83 \times 10^6$ daltons in molecular size derived from pRO1600 as carried along with RP1 in *Pseudomonas aeruginosa* NRRL-B-12125, wherein the plasmid derived from pRO1600 replicates itself upon cell division of the host bacterium because of deoxyribonucleic acid from pRO1600.

* * * * *

UNITED STATES PATENT AND TRADEMARK OFFICE
CERTIFICATE OF CORRECTION

PATENT NO. : 4,374,200
DATED : February 15, 1983
INVENTOR(S) : Ronald H. Olsen

It is certified that error appears in the above-identified patent and that said Letters Patent are hereby corrected as shown below:

Column 3, lines 35, 37 and 39 "PR1" should be --RP1--.

Column 6, line 18, "328" should be --238--.

Column 11, line 4, delete "is".

Column 11, line 23, "of" (first occurrence), should be --a--.

Column 12, line 19, "trasfer" should be --transfer--.

Column 12, lines 53 and 60 "PRO141" should be --PFO141--.

Column 13, line 6, "amine" should be --amino--.

Column 14, line 59 "borad" should be --broad--.

Signed and Sealed this

Twentieth Day of September 1983

[SEAL]

Attest:

GERALD J. MOSSINGHOFF

Attesting Officer     Commissioner of Patents and Trademarks